United States Patent [19]

Flaig et al.

[11] Patent Number: 5,067,359
[45] Date of Patent: Nov. 26, 1991

[54] APPARATUS FOR CLAMPING FLEXIBLE TUBES

[75] Inventors: Hans-Jürgen Flaig, Lauterbach; Paul Jahn, Frankfurt, both of Fed. Rep. of Germany

[73] Assignee: Fresenius AG, Bad Homburg Von der Hohe, Fed. Rep. of Germany

[21] Appl. No.: 548,165

[22] Filed: Jul. 3, 1990

[30] Foreign Application Priority Data

Jul. 19, 1989 [DE] Fed. Rep. of Germany ....... 3923837

[51] Int. Cl.$^5$ .................... F16H 21/44; F16K 31/02
[52] U.S. Cl. ......................................... 74/107; 74/569; 251/129.11; 251/254; 251/263
[58] Field of Search .............. 74/107, 57, 569; 251/6, 251/7, 129.11, 252, 253, 254, 255, 256, 262, 263

[56] References Cited

U.S. PATENT DOCUMENTS 2,074,240 3/1937 Saunders ........................ 251/254
2,679,165 5/1954 Montgomery ........................ 74/57
4,343,456 8/1982 Zitzloff ........................ 251/255
4,437,016 3/1984 Nakaya et al. ........................ 74/57 X

FOREIGN PATENT DOCUMENTS 1541363 4/1969 Fed. Rep. of Germany .
3104985 12/1981 Fed. Rep. of Germany .
3344849 6/1985 Fed. Rep. of Germany .
3403969 8/1985 Fed. Rep. of Germany .
355619 8/1961 Switzerland ........................ 74/107

Primary Examiner—Allan D. Herrmann
Assistant Examiner—David W. Laub
Attorney, Agent, or Firm—Townsend & Townsend

[57] ABSTRACT

An apparatus for clamping flexible tubing employs one or more plungers as clamps. The plungers are reciprocally moveable by means of a rotatable disk cam which has a cam path on one or both of the faces of the disk, the disk cam being mounted to rotate on a shaft of a stepping motor. The plungers may be used to clamp a single tube or a plurality of tubes.

23 Claims, 3 Drawing Sheets

APPARATUS FOR CLAMPING FLEXIBLE TUBES

BACKGROUND OF THE INVENTION

This invention relates to an apparatus for clamping flexible tubes, as is set forth in the preamble of the main claim and known from German patent specification 33 44 849 A1.

In the technical medical field, in particular in the case of extracorporeal circulations, it is often necessary to open or shut flexible tubes by means of clamps in a specific way. A typical example thereof is the dialysis with extracorporeal circulation using a single needle arrangement. During one operating cycle the flexible tube portions of the arterial and venous legs must respectively be opened or closed. This is carried out via corresponding clamps.

The clamping devices known from the prior art make use of lifting or rotary magnets which are operatively connected to a corresponding mechanism. These magnets have the great disadvantage that they consume a very great amount of power and lead to a considerable heat emission in the operative state. Another disadvantage of the magnets is the enormous noise which may disturb or affect patients, especially during dialyses that last for several hours.

German patent specification 33 44 849 A1 shows a safety means for infusion control devices wherein a flexible tube can be clamped by means of a sword which is displaceably supported in a direction transverse to the flexible tube. The sword is operated via a cam which is arranged on an output shaft of a gear system. The device serves as a safety means which is to have the particular effect that the infusion operation is interrupted in case of power failure. It follows therefrom that the device is not suited for continuously opening or closing a flexible tube during the infusion operation because the gear system itself as well as the stepping motor exhibit great inertia and cannot be designed without play in such a way that the valve function to be exerted by the sword is ensured in a reliable and quickly responding way.

German patent specification 31 04 985 A1 discloses a conveying or pumping apparatus wherein a flexible tube can be selectively clamped by means of two clamping elements, while a pump plunger with the aid of which the liquid volume between the two clamping elements can be displaced into the flexible tube is arranged in the area between the two clamping elements. With this apparatus a driving operation is carried out through a cam shaft which is provided with cams that are in operative communication with the pump element and the clamping elements respectively. This apparatus is not suited for exactly and reliably clamping a flexible tube of an infusion means because the clamping means are only intended for the pumping or conveying operation.

German patent application 15 41 363 discloses an infusion means in the case of which the flexible tube is clamped by means of a solenoid. As a consequence, this means has the disadvantages already mentioned in the introduction to the specification.

SUMMARY OF THE INVENTION

According to the invention, an apparatus is provided for clamping flexible tubing which employs one or more plungers as clamps. The plungers are reciprocally moveable by means of a rotatable disk cam which has a cam being mounted to rotate on a shaft of a stepping motor. The plungers may be used to clamp a single tube or a plurality of tubes.

It is the object of the invention to provide an apparatus for clamping flexible tubes, which apparatus is of a simple construction, employable in a reliable way and operable for a long period of time without having any adverse effects, above all on patients.

According to the invention this object is attained through the characterizing features of the main claim. The subclaims show other preferred embodiments.

The apparatus of the invention is characterized by a number of considerable advantages. Since plungers are used, it is possible to adapt the same to the respective cross-sections of the flexible tubes and to construct them in such a way that during operation of the apparatus the flexible tube is clamped or released in a reliable way. Since in accordance with the invention the plungers are operated via a cam element which is movable by means of a drive, the plungers can be biased towards and withdrawn from the flexible tube a purely mechanical way. The movement of the plungers is here not to be effected by electric drives: According to the invention it is only necessary to move the cam element itself. Since such a movement requires considerably smaller efforts than the clamping of the flexible tube, the driving power and thus the power consumption can be reduced to a considerable extent. According to the invention it is especially advantageous that the apparatus need only be acted upon with energy if there is a change in state, while no additional energy supply is required in stationary phases. Hence, the problems known from the prior art in connection with heat development and power consumption do not at all arise in the invention. Furthermore, a cam element can be moved in an almost noiseless way because only short displacement paths of the plungers are respectively required for opening or closing the apparatus. Another advantage of the cam element of the invention consists in that the element can be operated in an almost noiseless way as there are no sudden accelerations or decelerations of the armature elements as are known in the case of lifting magnets. The only noise that occurs in the apparatus of the invention is the running noise of the drive, e.g. an electric motor or a stepping motor which may additionally be provided with a gear system. As a result, the apparatus of the invention is especially suited for the long-time therapy of patients who are very sensitive to noise.

According to a preferred embodiment of the invention the cam element has the form of a rotatably supported cam disc. In accordance with the invention it is of course also possible to displace the cam element in the longitudinal direction, e.g. by using a rack-like drive. The rotatable configuration of the cam disc has the advantage that this disc can be of a very small and simple construction.

The cam disc of the invention is provided on at least one surface with a cam path which has elevated and recessed portions. The different levels between the elevated and recessed portions correspond to the longitudinal movement of the plungers, i.e. approximately to the diameter of the flexible tube. Hence, according to the invention the cam path controls the movement of the plungers in a direct way without necessitating the interposition of another gear system. Furthermore, it is ensured by the different levels between the elevated and recessed portions that each of the plungers is entirely moved over the necessary path length. Intermediate positions which might lead to malfunctions are thereby excluded.

The cam path is preferably of a circular or annular configuration. This has the advantage that the cam paths can be constructed in a very easy way and at low costs.

To make sure that the respective plunger is reliably guided along the cam element, the present invention suggests a plunger which is provided in its one end portion with a guide element that is movable along the cam path. This guide element is preferably a wheel which is rotatable about an axis arranged in a direction vertical to the longitudinal axis of the plunger and rolls along the cam path. There are only small frictional forces on account of the wheel. Furthermore, a virtually noiseless travel of the guide element is ensured.

To guarantee an exact movement of the cam path, the drive is preferably designed in the form of a stepping motor. It is thus possible to move the circular cam path in a rotating way or to rotate it back and forth in a reversing way.

Since in the apparatus of the invention a forced movement of the plunger is necessary in both directions of movement, there are various possibilities of construction. It is e.g. possible to bias the plunger by means of an elastic biasing element in one motional direction, while movement in the other motional direction is effected via the cam element. The biasing operation can be carried out such that the plunger is biased in the closing position; it is also possible to bias the plunger in the opening position. Biasing in the closing position has the essential advantage that the flexible tube is exactly clamped because slight permissible variations of the diameter of the flexible tube or the like can be compensated by the elastic biasing element.

According to an alternative embodiment of the invention it is also advantageous to move the plunger in both directions of movement via the cam element; the cam path can e.g. be shaped like a lateral groove of the cam element. A plate-like configuration of the cam element is also possible. The cam element is here provided with a cam path at both sides, with one side of the cam element respectively corresponding to one motional direction of the plunger.

In accordance with the invention the forced guidance of the respective plungers determines the movement thereof, so that additional control measures do normally not become necessary. According to the invention it is however advantageous for various modes of application if the support has additionally arranged thereon a sensor element with the aid of which the position of the plunger, or in another modification the position of the cam path, can be determined. The sensor element may e.g. be designed as a light barrier.

A plurality of plungers can be mounted in the apparatus of the invention, so that a multitude of flexible tubes of an extracorporeal circulation can be clamped or released by means of a single apparatus as set forth in the invention. It is here of special advantage that only one stepping motor is required for operating a cam element which can be used for displacing several plungers at the same time. The plungers may be in engagement with different portions of the cam path. It is also possible to keep a plurality of plungers in engagement with the same portion of the cam path. In the latter case the plungers are no longer operable individually and independently of each other, but the associated plungers are respectively moved upwards or downwards at the same time.

In another embodiment of the invention it is also possible to clamp a flexible tube with the aid of each plunger or to construct the plungers such that a plurality of flexible tubes which are e.g. arranged next to one another can be clamped or released by said plungers. Furthermore, the apparatus permits the operation of a plurality of cam elements and plungers by means of a single drive.

BRIEF DESCRIPTION OF THE DRAWINGS

The present invention shall now be with the aid of embodiments with reference to the drawing, in which.

DESCRIPTION OF SPECIFIC EMBODIMENTS

Figure 1:
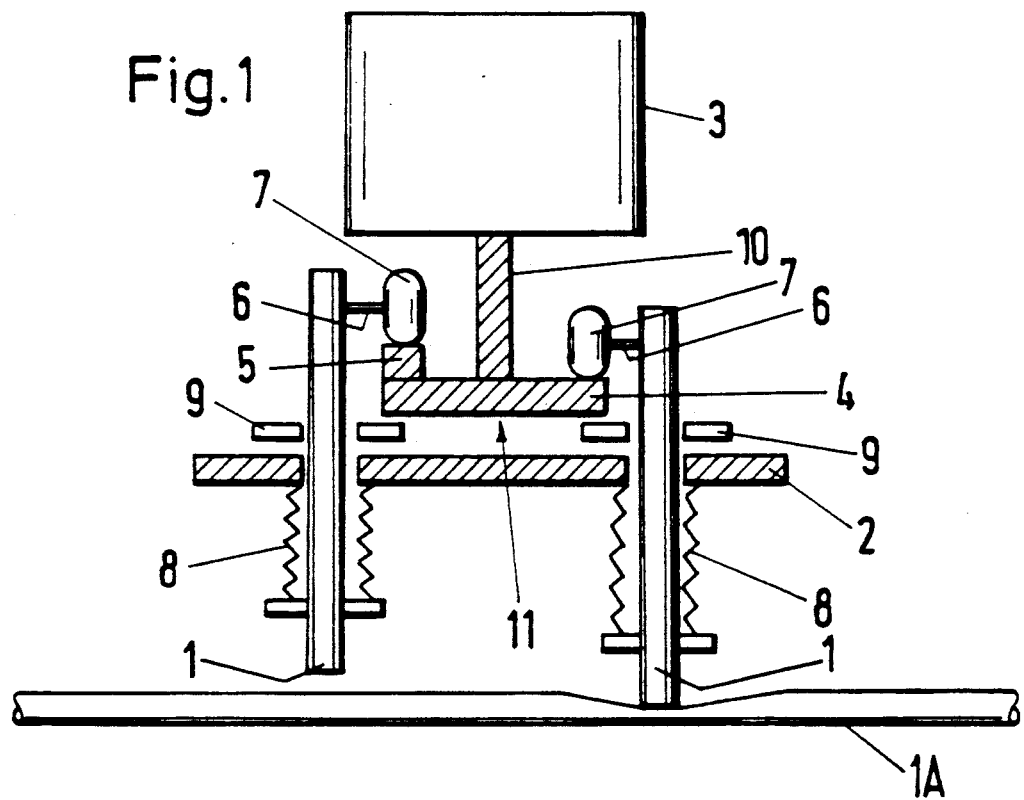
FIG. 1 is a diagrammatic side view of a first embodiment of the apparatus of the invention.

The apparatus of the invention comprises a support 2 which is only shown in a diagrammatic way in FIG. 1. Support 2 comprises a plurality of plungers 1 which are of bar- or rod-shaped configuration and can respectively be urged in their lower end portion towards a flexible tube. For reasons of simplification FIG. 1 does not show the construction of the lower ends of the plungers which may be adapted to the flexible tubes in a specific way.

Plungers 1 which are slidably carried on support 2 are provided in their upper end portion with an axis 6 which is arranged in a direction transverse to the longitudinal direction of plunger 1 and rotatably carries a guide element 7 which is shaped like a wheel.

Furthermore, support 2 is provided with respective sensor elements 9 which may e.g. be designed in the form of a light barrier or the like to detect the respective position of plunger 1. Furthermore, support 2 is provided with a sensor element 11 which may e.g. be designed in the form a reflecting light barrier to detect the position of cam disc 4.

A drive (stepping motor) 3 is provided above carrier 2. Its axis 10 carries at its lower end a cam disc 4 which is provided with a circular or annular cam path 5. Wheels 7 of plungers 1 travel along cam path 5, so that a rotating operation of cam disc 4 effects an upward or downward movement of the plungers.

Since in the shown embodiment the plungers are only guided by cam path 5 in an upwardly directed path of travel, a biasing element 8 is respectively provided below support 2 in the form of a pressure spring. This spring biases plunger 1 into a clamping position, as illustrated in the right half of FIG. 1. The left half of FIG. 1 shows plunger 1 in its retracted state.

Figure 2:
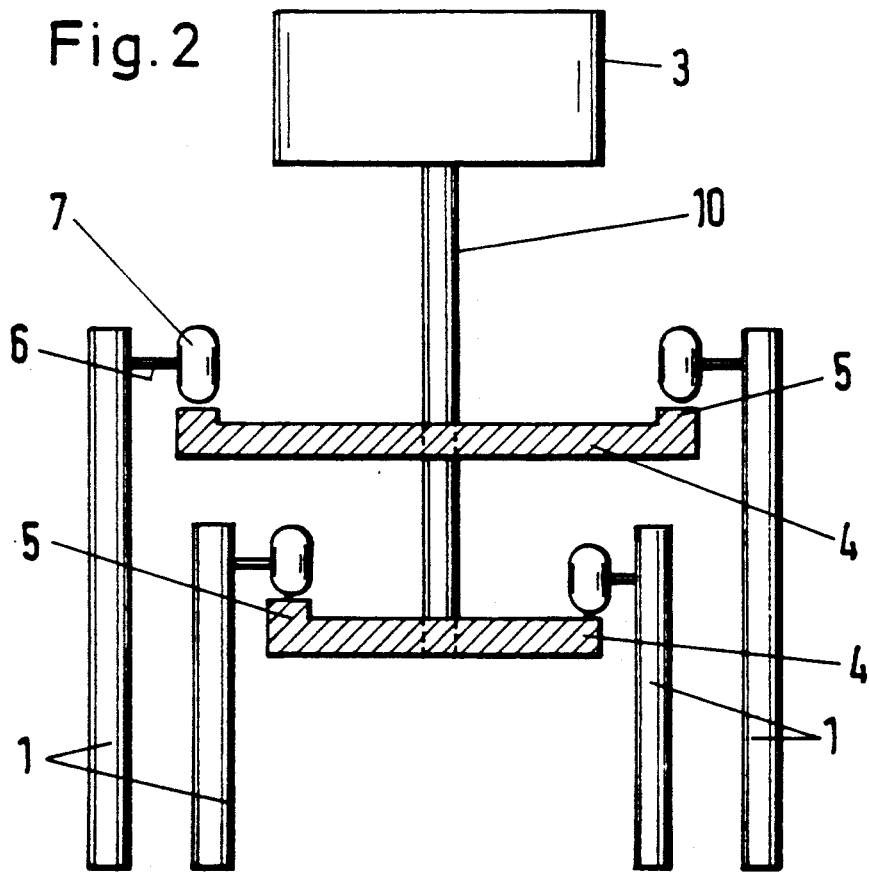
FIG. 2 is a diagrammatic partial view of a modified embodiment of the apparatus shown in FIG. 1.

The embodiment shown in FIG. 2 differs from the embodiment of FIG. 1 in that axis 10 is provided with two cam discs 4 which respectively comprise a cam path 5 and serve to operate two respective plungers 1.

It is obvious to one skilled in the art that the invention is not restricted to the presence of two plungers; it is also possible to employ only one plunger or a plurality of plungers.

The respective position of the plungers can be monitored in response to the rotary position of cam disc 4 or by sensor element 9. Monitoring with the aid of the sensor element has the advantage that in case of failure, e.g. breakage of biasing element 8, the fault can immediately be detected.

The use of a stepping motor has the advantage that this motor only requires a very small amount of holding current which normally accounts for only about 20% of the operating current.

The apparatus of the invention permits the individual and independent movement of the respective plungers 1. As has already been mentioned, the circular cam disc 4 is therefore provided with a circular or annular cam path 5 whose elevations and recessed portions respectively pass into one another via suitable inclined surfaces so as to facilitate the rolling movement of guide element 7.

Figure 3:
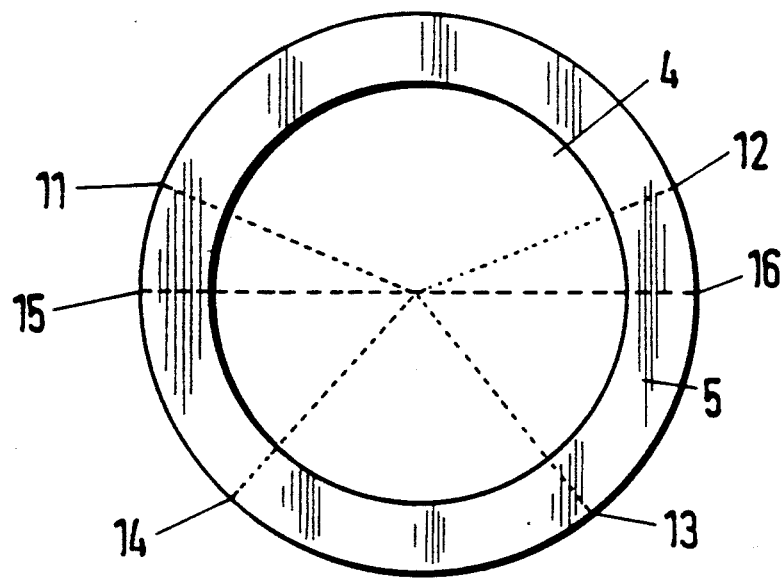
FIG. 3 is a top view on a cam element of the invention.
Figure 4:
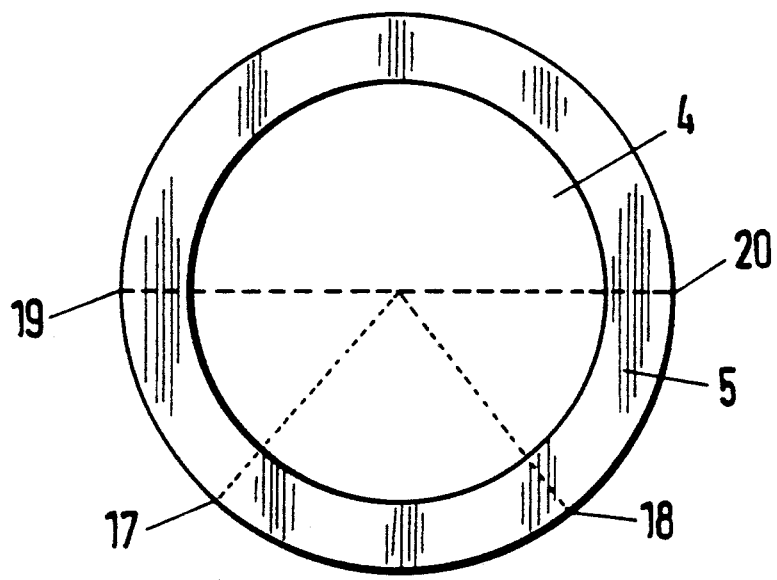
FIG. 4 is a top view on another cam element of the invention.

Both FIG. 3 and FIG. 4 show top views on different embodiments of a cam disc of the invention. The embodiment illustrated in FIG. 3 relates to two plungers 1. Cam path 5 includes elevated and recessed portions, as is diagrammatically shown in FIG. 1. In this embodiment an elevation of the cam path is provided between points 11 and 12; another elevation of a reduced size is located between points 13 and 14. The height of the elevation of cam path 5 follows from the greatest possible and desired stroke of plunger 1. In an advantageous embodiment the longer elevated portion is provided between points 11 and 12 in an angular portion of 105°, while the shorter portion extends over an angle of 50°. The ascent at the right and left sides, which is required for obtaining the respective elevation, covers an angle of 30°. In the illustrated embodiment the difference in level between the elevated and lowered portions amounts to 3 mm, so that the plunger can be raised or lowered by 3 mm on the whole. In the 0 position of the cam disc the respective wheels 7 are at points 15 and 16. These points represent lowered portions in which the respective flexible tubes are clamped.

At the beginning of the operation the 0 position of the cam disc is made use of. The plunger which is shown at the right side in FIG. 1 is withdrawn by clockwise rotating the cam disc by 45°. The plunger which is shown at the left side in FIG. 1 is also withdrawn by a further rotation of 45° in the same direction. After a backward rotation by the same angle the left plunger is extended again; another backward rotation results in an extension of the right plunger. On account of the symmetry of the cams it is also possible to move the plungers in the reverse order by reversing the direction of rotation from the 0 position.

FIG. 4 shows another embodiment in which an elevation of the cam path is provided between points 17 and 18. The elevation consists of a ramp having an angle of 30° and a plateau which extends over an angle of 15°. At the beginning of the operation the 0 position is made use of (points 19 and 20). A clockwise rotation of the cam disc by 90° lifts the plunger shown at the left side in FIG. 1, while the plunger shown at the right side in FIG. 1 is lifted from the 0 position by a counterclockwise rotation of the same angular amount. With this embodiment it is always ensured that at least one of the two clamps is closed.

The apparatus of the invention permits the separate and independent operation of the individual plungers and makes it possible to assign the movement of the plungers in such a way that a corresponding functional sequence of the respective system is ensured. Since a plurality of plungers are respectively operated by a cam path, it is ensured at the same time that the movements of the two plungers are matched to each other. Failure of only one plunger, as is sometimes the case with lifting magnets, is here excluded. This considerably improves the operational reliability.

The most different motional sequences of the plungers can be attained by suitably arranging plungers 1 on the circumference of cam disc 4. A compact construction is obtained in addition to the low power consumption and low heat development of the apparatus of the invention. Furthermore, the operation of the apparatus of the invention is virtually noiseless. The mechanical coupling of the plungers considerably increases the operational reliability.

Figure 5:
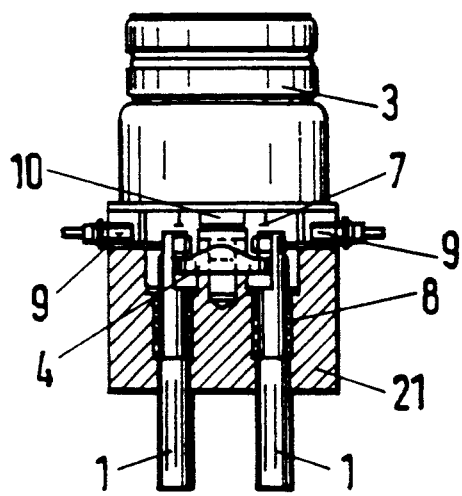
FIG. 5 is another side view, similar to FIG. 1, of an embodiment of the apparatus of the invention.

FIG. 5 is a side view, partly sectional view, of another embodiment of the apparatus of the invention. Same parts are designated by the same reference numerals. As becomes apparent from the illustration in FIG. 5, plungers 1 are guided in bores of a housing 21, with plungers 1 being of a stepped configuration and surrounded by helical spring 8 (biasing element) in their upper portion having a reduced diameter. Driving motor 3 is flange-mounted on the upper side of housing 21. The sensor means are laterally inserted into housing 21.

Figure 6:
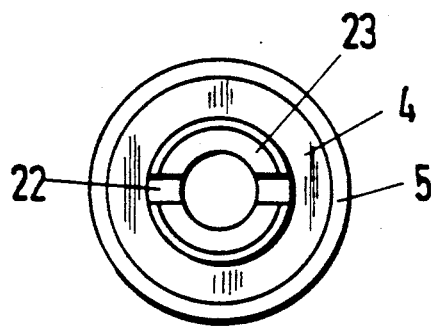
FIG. 6 is a top view on the embodiment of the cam disc as shown in FIG. 5.
Figure 7:
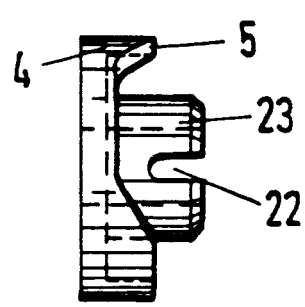
FIG. 7 is a side view of the cam disc shown in FIG. 6 on the left side of FIG. 6.
Figure 8:
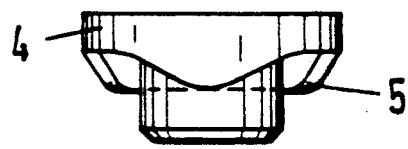
FIG. 8 is a side view of the embodiment of the cam disc shown in FIG. 6 on the upper side of FIG. 6.

FIGS. 6–8, of which one is a top view and the two others are a side view, show an embodiment of cam disc 4 provided with a cam path 5. It becomes apparent from this embodiment that cam disc 4 is provided with a hub 23 which is transversely crossed by a groove 22. Groove 22 makes it possible that in a specific position of cam disc 4 the two sensors 9 (see FIG. 5) are capable of transmitting an optical signal (transmitter and receiver) so as to determine the rotary position of cam disc 4.

Figure 9:
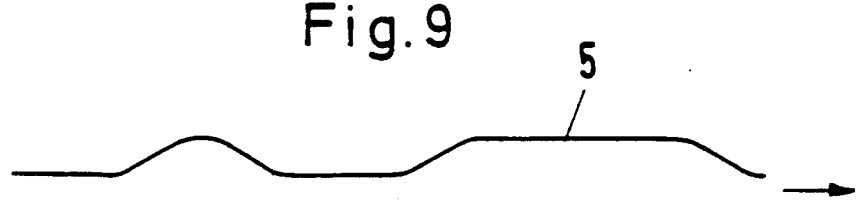
FIG. 9 is a developed view of the cam path of the cam disc shown in FIGS. 6–8.

FIG. 9 shows a developed view of the cam path illustrated in FIGS. 6–8, with the arrow directed towards the right marking the rolling travel line or direction.

The present invention is not limited to the illustrated embodiments. Many modifications and alterations are possible within the scope of the invention and obvious to one skilled in the art.

We claim:

1. An apparatus for clamping flexible tubes comprising:
   at least one plunger means longitudinally displaceable along a first longitudinal axis, said plunger means adapted to be biased in a first longitudinal direction;
   at least one support means; and
   at least one cam element rotatably movable by drive means for longitudinally moving said plunger along said first longitudinal axis, said cam element comprising a cam disc adapted to rotate about a second longitudinal axis parallel to said first longitudinal axis of said plunger means, said cam disk having on at least one surface a cam path having elevated and recessed portions for interacting with said plunger means.

2. An apparatus according to claim 1, wherein said cam path defines an annular configuration.

3. An apparatus according to claim 1, wherein said plunger means is provided on one end portion with a cam following guide element for tracking said cam path.

4. An apparatus according to claim 3, wherein said cam follower guide element is a rotatable wheel, said wheel being connected to said plunger means through an axle extending laterally from said end portion of said plunger means.

5. An apparatus according to claim 1, wherein said drive means comprises a stepping motor.

6. An apparatus according to claim 1, further comprising an elastic biasing element for biasing said plunger means in said first longitudinal direction along said first longitudinal axis opposing said cam surface such that movement of said plunger means is effected via said cam element.

7. An apparatus according to claim 6, wherein said plunger means is moveable between a first clamping position and a second open position, said plunger means being biased by said biasing element toward said first clamping position.

8. An apparatus according to claim 6, further comprising a second biasing element, wherein, in the second open position, said plunger means is biased by said second biasing element away from said first clamping position.

9. An apparatus according to claim 1, wherein said plunger means is movable by means of said cam element in both directions of movement.

10. An apparatus according to claim 9, characterized in that said cam path is constructed as a lateral groove on said cam element.

11. An apparatus according to claim 9, wherein said cam element is formed on a plate-like structure and is provided upon opposing surfaces with cam paths, the longitudinal displacement of said plunger means being influence by both cam paths.

12. An apparatus according to claim 11, further comprising a first sensor element arranged on said support for determining the position of said plunger.

13. An apparatus according to claim 12, wherein said sensor element forms a light barrier.

14. An apparatus according to claim 12, further comprising a second sensor element is arranged on said support for determining the position of said cam disc.

15. An apparatus according to claim 14, wherein said second sensor element forms a light barrier.

16. An apparatus according to claim 1, wherein a plurality of said plunger means are provided.

17. An apparatus according to claim 16, wherein said plurality of said plunger means are disposed to be in engagement with different portions of said cam path.

18. An apparatus according to claim 16, wherein a plurality of said plunger means are disposed to be in engagement with a common portion of said cam path.

19. An apparatus according to claim 16, wherein each of said plunger means (1) is for clamping a single common flexible tube.

20. An apparatus according to claim 16, wherein each of said plunger means is for claiming individual flexible tubes.

21. An apparatus according to claim 1, wherein said cam disc is rotatable in a circle.

22. An apparatus according to claim 1, wherein said cam disc can be rotatably reciprocated by predetermined angular amounts.

23. An apparatus according to claim 1, wherein a plurality of cam elements and plunge means are actuatable my means of a common drive means.

* * * * *